(12) United States Patent
Morris et al.

(10) Patent No.: US 7,413,564 B2
(45) Date of Patent: Aug. 19, 2008

(54) SLIT VALVE CATHETERS

(75) Inventors: Mary M. Morris, Mounds View, MN (US); Timothy G. Laske, Shoreview, MN (US); Kenneth T. Heruth, Edina, MN (US); Michael R. Ujhelyi, Maple Grove, MN (US); Jesus W. Casas-Bejar, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/382,948

(22) Filed: Mar. 6, 2003

(65) Prior Publication Data

US 2004/0176743 A1 Sep. 9, 2004

(51) Int. Cl.
*A61M 25/16* (2006.01)
*A61M 25/18* (2006.01)

(52) U.S. Cl. .................. 604/537; 604/288.01

(58) Field of Classification Search ........... 604/523, 604/528, 537, 288.01–288.04
See application file for complete search history.

(56) References Cited

U.S. PATENT DOCUMENTS

| | | | | |
|---|---|---|---|---|
| 3,726,283 A * | 4/1973 | Dye et al. | | 604/99.03 |
| 4,319,580 A * | 3/1982 | Colley et al. | | 600/453 |
| 4,382,445 A * | 5/1983 | Sommers | | 604/8 |
| 4,431,426 A * | 2/1984 | Groshong et al. | | 604/523 |
| 4,549,879 A | 10/1985 | Groshong et al. | | |
| 4,671,796 A | 6/1987 | Groshong et al. | | |
| 4,973,319 A | 11/1990 | Melsky | | |
| 5,147,332 A * | 9/1992 | Moorehead | | 604/247 |
| 5,250,034 A | 10/1993 | Appling et al. | | |
| 5,261,885 A * | 11/1993 | Lui | | 604/247 |
| 5,304,155 A * | 4/1994 | Lui | | 604/247 |
| 5,522,807 A * | 6/1996 | Luther | | 604/264 |
| 5,807,349 A * | 9/1998 | Person et al. | | 604/247 |
| 5,928,203 A | 7/1999 | Davey et al. | | |
| 5,984,903 A | 11/1999 | Nadal | | |
| 2002/0156430 A1* | 10/2002 | Haarala et al. | | 604/247 |
| 2005/0043703 A1* | 2/2005 | Nordgren | | 604/500 |
| 2005/0283122 A1* | 12/2005 | Nordgren | | 604/247 |

FOREIGN PATENT DOCUMENTS

FR 2707505 A1 * 1/1995
WO WO 01/74434 A2 * 10/2001

* cited by examiner

*Primary Examiner*—Kevin C. Sirmons
*Assistant Examiner*—Andrew M Gilbert
(74) *Attorney, Agent, or Firm*—Michael C. Soldner; Stephen W. Bauer

(57) ABSTRACT

An external surface of a catheter body includes a pressure responsive slit formed in an indentation wherein a wall thickness of the catheter body within the indentation is less than a wall thickness of a major portion of the catheter body. Material exits a lumen of the catheter body, via the pressure responsive slit, when a pressure inside the lumen exceeds an external pressure.

19 Claims, 5 Drawing Sheets

SLIT VALVE CATHETERS

CROSS-REFERENCE TO RELATED APPLICATION

Cross-reference is hereby made to commonly assigned related U.S. application Ser. No. 10/382,757 to Mary Morris et al, filed concurrently herewith entitled "Sleeve Valve Catheters" and issued on Jun. 26, 2007 as U.S. Pat. No. 7,234,067.

TECHNICAL FIELD

The invention relates to slit valve catheters for administration of material into a body of a patient.

BACKGROUND

Medical catheters are used for the administration of therapeutic agents or nutrients into a body of a patient. A medical catheter is inserted into the body and, more particularly, either into a moderate to large vessel within the body or a body cavity or space. The catheter includes an exit port to deliver a solution, which may include nutrients, therapeutic agents, or a combination thereof from a lumen of the catheter to the body.

Conventional catheters include at least one pressure responsive valve, such as a slit valve. A slit valve may, for example, be formed by cutting one or more slits in a wall of a catheter. The pressure responsive valve opens in response to pressure gradients to permit fluid flow through the catheter. More specifically, when the pressure differential exceeds a threshold of the slit valve, the catheter walls defining the slit protrude and allow fluid to flow through the catheter.

Depending on whether the pressure differential is negative or positive, fluid may travel from the patient to the catheter or from the catheter to the patient. A negative pressure differential occurs when the pressure level inside the catheter decreases below the pressure level outside of the catheter. A slight negative pressure differential tends to close the slit, however a larger differential causes the slit to open inward. A positive pressure differential occurs when the pressure level inside the catheter increases above the pressure differential outside of the catheter. A positive pressure differential opens the slit outward.

At neutral pressures, i.e., the pressure level inside and outside of the catheter are substantially the same, the catheter walls defining the slit form a seal to prevent fluid flow into or out of the catheter. In other words, the catheter closes at neutral pressures. The pressure differential needed to open the slit valve may vary depending on the number of slits in the catheter, the length of the slits, the thickness of the catheter wall or the elasticity of the catheter wall.

Some patients may require an implanted catheter for an extended period of time. However, catheters that remain implanted in a body of a patient may become occluded over time due to blood ingression, thrombus formation or fibrous tissue encapsulation. When a catheter does become occluded, the patient will not receive the necessary therapeutic agents or nutrients. In this case, the catheter must be removed and either cleaned or replaced with a new catheter.

DETAILED DESCRIPTION

Figure 1:
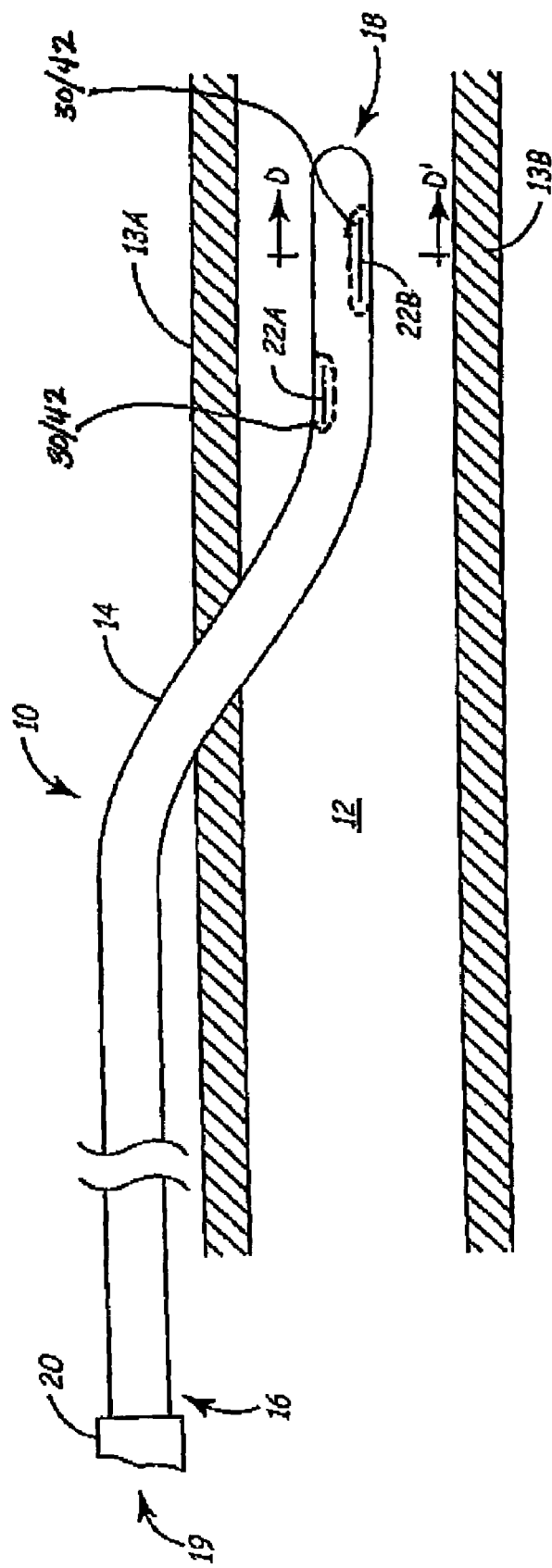
FIG. 1 is a schematic diagram illustrating a slit valve catheter.

FIG. 1 is a schematic diagram illustrating a slit valve catheter 10 for administration of therapeutic agents or nutrients into a body of a patient. Slit valve catheter 10 is inserted into the body of the patient and, more particularly into a vessel 12 of the patient, defined by vessel walls 13A and 13B ("vessel walls 13"). Slit valve catheter 10 infuses fluid or other material into the blood stream flowing through vessel 12. Although in the example of FIG. 1 slit valve catheter 10 is implanted within vessel 12, slit valve catheter 10 may be implanted within other body lumens, cavities, or spaces such as the brain ventricle.

In the example of FIG. 1, slit valve catheter 10 includes a catheter body 14 with a proximal end 16 that resides outside of the body of the patient and a distal end 18 that is implanted within vessel 12. In other embodiments, proximal end 16 may be within the body and coupled to an implanted drug delivery device or a catheter access port. As illustrated in FIG. 1, Slits 22A and 22B ("slits 22") are formed in distal end 18 to serve as pressure responsive valves. Slit valve catheter 10 receives a material, such as a fluid, via an opening 19 at proximal end 16 and delivers the material out from slit 22A or slit 22B or both slits 22. The material, for example, may be a solution that includes therapeutic agents, nutrients, or a combination thereof to be delivered to the body of the patient. According to embodiments of the present invention, proximal end 16 includes a fitting 20 that couples to a source of the material or a device for injecting the material into the body of the patient. Types of fitting 20 include a quick-connect fitting and a luer lock fitting, and the type of material source to which fitting 20 is coupled includes a syringe, a pump and other injection devices.

Distal end 18 of catheter body 14 may be tapered to reduce the likelihood of thrombus formation at distal end 18. Thrombus formation generally occurs in regions of turbulence and/or stagnancy in the blood flow, which leads to clotting. In the example of FIG. 1, distal end 18 of catheter body 14 is rounded to reduce the amount of blood flow turbulence and stagnancy. However, distal end 18 may be tapered differently. For instance, distal end 18 may have a linear or nonlinear taper. Catheter body 14 may be closed at distal end 18 in order to build up pressure within catheter body 14 to open a pressure responsive valve. At least a portion of catheter body 14 may be translucent so that a physician can visually determine the presence of air bubbles, blood, or other liquids within catheter body 14.

According to one embodiment of the present invention, catheter body 14, away from slits 22, is constructed of a non-compliant polymer to prevent catheter body 14 from expanding, or 'ballooning', which increases the liquid volume and pressure necessary to open slits 22. A non-compliant material from which catheter body 14 is constructed is selected from a group of biocompatible materials including polyurethane, fluoropolymer, polyimide, polyamide, polypropylene, and polyethylene. In an alternate embodiment, catheter body 14 is constructed of a silicone. In this case, catheter body 14 includes an overlay or a liner to limit the compliance of catheter body 14 to prevent catheter body 14 from 'ballooning' due to a pressure increase.

Slits 22 are defined by two slit surfaces that are normally abutted to form a seal between vessel 12 and inside catheter body 14. In accordance with one embodiment of the present invention, catheter body 14 is indented proximate slits 22 when unpressurized. The term "unpressurized" generally refers to a neutral pressure level inside and outside of catheter body 14.

Upon becoming pressurized, the indented portion of catheter body 14 protrudes outward to separate the two slit surfaces, in turn, opening the respective slit 22. The term "pressurized" generally refers to an increase in the pressure level within catheter body 14, which causes a positive pressure differential between inside catheter body 14 and outside catheter body 14.

Slit valve catheter 10 infuses the therapeutic agents or nutrients into the body of the patient via slits 22. When catheter body 14 becomes unpressurized again, the two slit surfaces of the respective slit 22 once again become abutted to form a seal to prevent fluid flow to and from catheter body 14. Further, catheter body 14 once again becomes indented proximate the respective slit 22.

Although slits 22 of slit valve catheter 10 have been described as one-way pressure responsive valves, i.e., for infusing material into the body of the patient, according to another embodiment of the present invention, slits 22 function as two-way pressurized valves, opening inward due to a negative pressure differential to aspirate fluids from vessel 12 as well as opening outward to infuse fluids to vessel 12.

For example, the application of suction or vacuum pressure to the catheter creates a negative pressure differential, i.e., the pressure outside of catheter body 14 exceeds the pressure inside catheter body 14. When the negative pressure differential exceeds a threshold negative pressure differential, catheter body 14 proximate slits 22 collapses, causing the slit surfaces to separate and, in turn, form an opening through which fluid may be withdrawn from vessel 12.

In the example illustrated in FIG. 1 slit valve catheter 10 has two slits 22. However, according to alternate embodiments, slit valve catheter 10 has either a single slit 22 or more than two slits 22. Slits 22 may be designed and arranged to provide infusion redundancy. In other words, according to one embodiment of the present invention, one of slits 22 may be a primary slit while the other slit functions as a surrogate slit. For example, slit 22B is the primary slit, i.e., the slit through which material usually exits catheter body 14 and slit 22A is the surrogate slit, i.e., the slit through which material exits catheter body 14 when the material may no longer exit via the primary slit. Material may not be able to exit via the primary slit, i.e., slit 22B, due to blood ingression, thrombus formation, or fibrous tissue encapsulation.

In order to have one of slits 22 function as a primary slit and one of slits 22 function as a surrogate slit, slits 22 need to be formed such that each of slits 22 opens at slightly different pressure differentials. In one embodiment, slit 22B is a longer slit than slit 22A so that slit 22B opens at a lower pressure differential. Alternatively, catheter body 14 may be thinner proximate to slit 22B.

In another embodiment according to the present invention, catheter body 14 is chemically treated near slit 22B to weaken the catheter body 14, in turn, making catheter body 14 near slit 22B more compliant. For example, soaking a portion of catheter body 14 surrounding slit 22B in silicone oil chemically weakens catheter body 14 near slit 22B. The increased compliance lowers the pressure differential needed to open the slit valve. Slits 22 are straight slits that are parallel with a longitudinal wall of catheter body 14. However, slits 22 may be angled with respect to the longitudinal wall of catheter body 14, perpendicular to the longitudinal wall of catheter body 14, or have a different orientation or shape. Further, a combination of slits with different orientations and shapes may be utilized.

Slits 22 may be displaced relative to one another to reduce the likelihood that both slits 22A and 22B will become occluded due to thrombus formation or fibrous tissue encapsulation at the same time. Slits 22 may be longitudinally displaced relative to one another along a length of catheter body 14. Alternatively, slits 22 may be circumferentially displaced relative to one another along a circumference of catheter body 14. Further, slits 22 may be both longitudinally and circumferentially displaced relative to one another. Longitudinally and/or circumferentially displacing slits 22 relative to one another prevents structurally weakening catheter body 14 by not placing a multitude of slits in a single radial or longitudinal plane.

According to one embodiment of the present invention, slit valve catheter 10 further includes a coating that elutes a therapeutic agent. The coating may be on an exterior surface of catheter body 14 or an interior surface of catheter body 14. Agents eluted from the coating include drugs, proteins, and genes adapted to reduce the likelihood of thrombus formation or fibrous tissue encapsulation. For example, the exterior portion of slit valve catheter 10 includes a coating of Heparin to reduce the likelihood of thrombus formation.

Slit valve catheter 10 performs as any of a number of catheters for administration of therapeutic agents or nutrients into a body of a patient, for example, a central venous catheter, a vascular catheter, an intra-cerebral ventricular catheter, a pericardial catheter, an intrathecal catheter, or an epidural catheter. The different catheters may vary in size and shape depending on the application. For example, a catheter that is placed in a smaller vessel may need to have a smaller diameter than a catheter that is placed in a larger vessel.

Figure 2A:
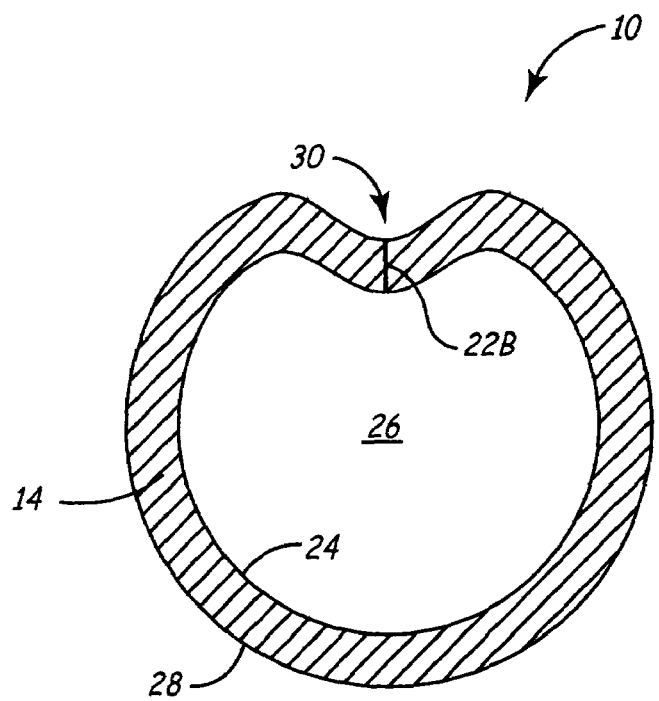
FIGS. 2a and 2b are a cross-section end view illustrating slit valve catheter of FIG 1.

FIG. 2 is a cross-sectional end view illustrating slit valve catheter 10 of FIG. 1 from D to D'. Catheter body 14 has a first wall thickness and includes an interior surface 24 that defines a lumen 26 and an exterior surface 28 exposed to an environment within a body of a patient. Slit valve catheter 10 includes a slit 22B cut into catheter body to function as a pressure responsive valve. Slit 22B is defined by two slit surfaces that are normally abutted to form a seal that restricts fluid flow between vessel 12 and lumen 26. FIG. 2(A) illustrates slit valve catheter 10, in an unpressurized state, including an indentation 30 formed in a portion of catheter body 14. Slit 22B is formed in the indentation. According to one embodiment of the present invention, indentation 30 decreases a compliance of catheter body 14 in proximity to slit 22B, causing slit 22B to be more responsive to pressure differentials. The pressure level at which slit 22B opens depends on the properties of catheter body 14 and slit 228, such as the compliance of catheter body 14 adjacent slit 22B, the length of slit 22B, and the like. For example, according to one embodiment, catheter body 14 has a thickness adjacent slit 22B that is less than the first wall thickness, which increases the compliance of catheter body 14 adjacent slit 228. In this manner, slit 22B opens at a lower applied pressure differential due to the increased compliance of catheter body 14 adjacent slit 22B.

Figure 2B:
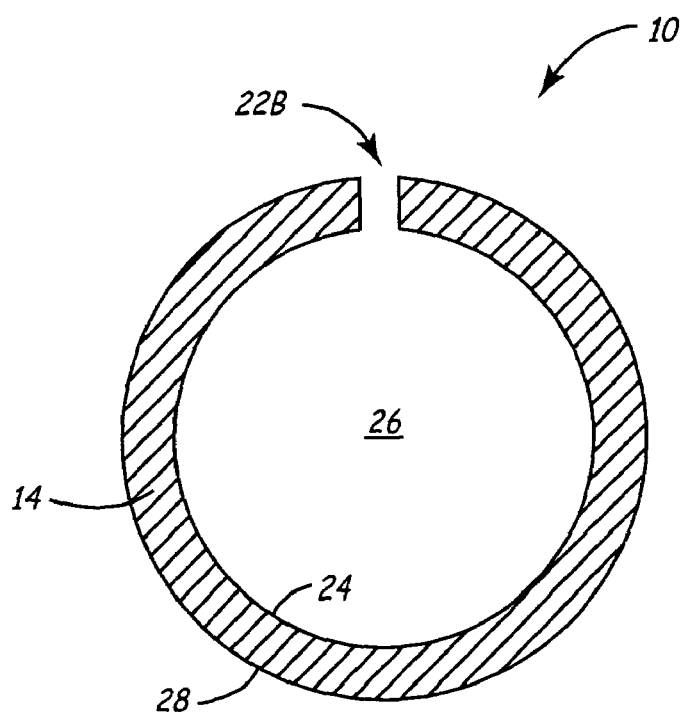

FIG. 2(B) illustrates slit valve catheter 10 in a pressurized state in which a large enough pressure differential exists to overcome the force of normally abutted slit surfaces and thereby open slit valve catheter 10, allowing slit valve catheter 10 to infuse fluid into the body of the patient. Upon becoming pressurized, indent 30 of catheter body 14 protrudes outward to open the respective slit 22B. More specifically, as indent 30 of catheter body 14 protrudes outward, the slit surfaces that define slit 22B separate to form an opening through which material may exit lumen 26. According to one embodiment of the present invention, the surfaces defining slit 22B include a coating formed from an anti-blocking agent, for example graphite or talc. Blocking, defined as a cross-linking between the surfaces as a function of time and temperature, can cause the surfaces to stick together.

In the example of FIG. 2, lumen 26 of slit valve catheter 10 has a cylindrical shape. However, slit valve catheter 10 and lumen 26 may be geometrically formed to take any shape. For example, slit valve catheter 10 may comprise a D-shaped lumen.

Figure 3:
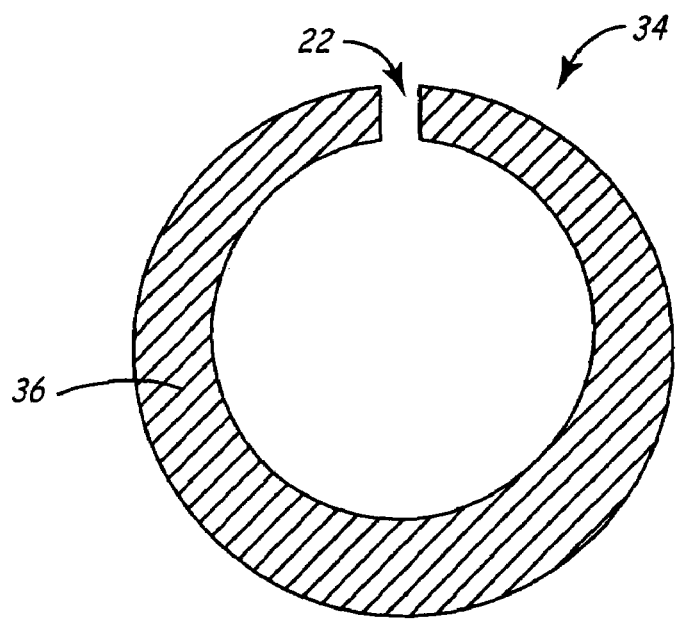
FIG. 3 is a cross-sectional end view illustrating an exemplary slit valve catheter with a non-uniform thickness.

FIG. 3 is a cross-sectional end view illustrating an exemplary slit valve catheter 34 according to another embodiment of the present invention. In the example illustrated in FIG. 3, slit valve catheter 34 is pressurized. As illustrated in FIG. 3, a thickness of catheter body 36 proximate a slit 22 is less than the thickness of a major portion of catheter body 36. The reduced thickness of catheter body 34 proximate slit 22 makes catheter body 34 proximate slit 22 more compliant and decreases the pressure differential needed to separate the slit surfaces that define slit 22. In this manner, the thickness of catheter body 36 may be adjusted in order to adjust the pressure differential required to open slit 22.

Figure 4:
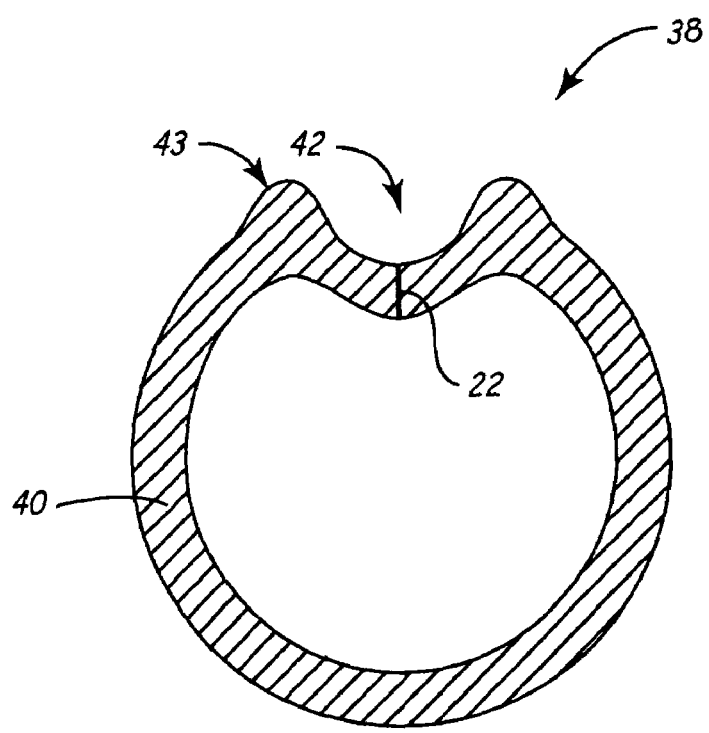
FIG. 4 is a cross-sectional end view illustrating another exemplary slit valve catheter with a non-uniform thickness.

FIG. 4 is a cross-sectional end view illustrating another exemplary slit valve catheter 38 with a non-uniform thickness. In the example illustrated in FIG. 4, slit valve catheter 38 is un-pressurized. As illustrated in FIG. 4, catheter body 40 has a first wall thickness, includes an indent 42, and further has a non-uniform wall thickness wherein the thickness of a portion 43 surrounding slit 22 is greater than the first wall thickness. Portion 43 surrounding slit 22 serves to stiffen a hinge-like structure created by indentation 42, thereby fine tuning the pressure responsiveness of slit 22.

Figure 5:
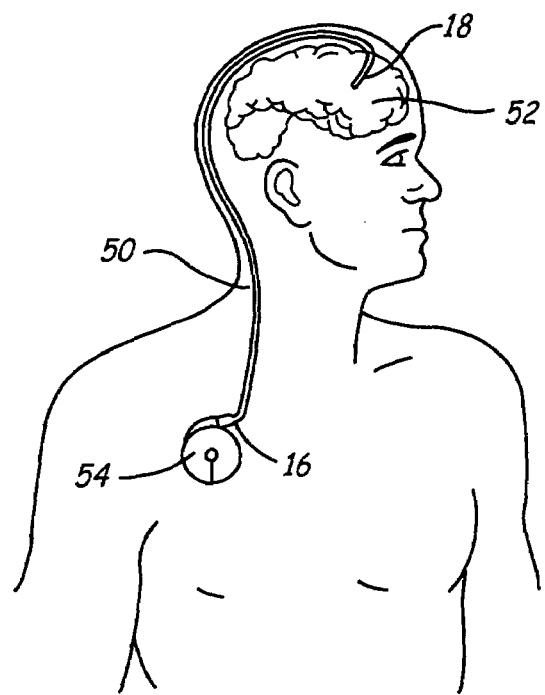
FIG. 5 is a schematic diagram illustrating an implanted catheter including a slit valve according to one embodiment of the present invention.

FIG. 5 is a schematic diagram illustrating an implanted catheter including a slit valve according to one embodiment of the present invention. As illustrated in FIG. 5, a slit valve catheter 50 includes a distal end 18 implanted within a brain 52 and a proximal end 16 coupled to an implanted pump 54. Catheter 50 further includes at least one slit valve, conforming to any of the embodiments described herein, near distal end 18 for delivery of therapeutic agents or nutrients from pump 54 to brain 52. An alternate embodiment of catheter 50 is further described in conjunction with FIG. 14.

Figure 6:
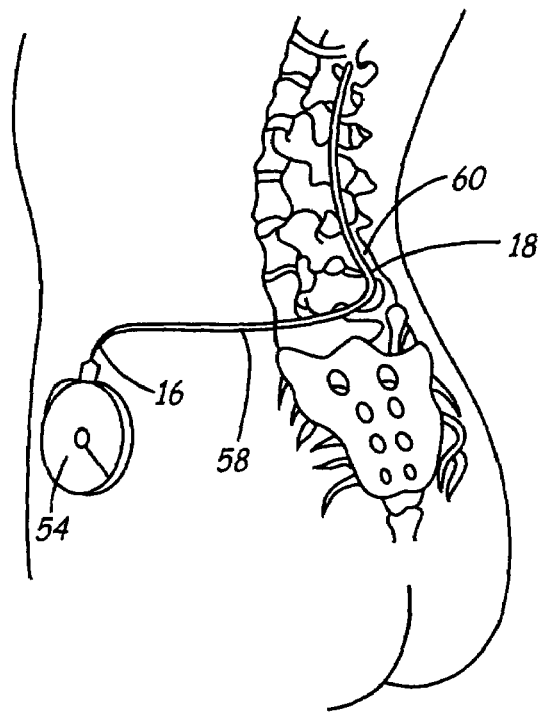
FIG. 6 is a schematic diagram illustrating an implanted catheter including a slit valve according to another embodiment of the present invention.

FIG. 6 is a schematic diagram illustrating an implanted catheter including a slit valve according to another embodiment of the present invention. As illustrated in FIG. 6, a sleeve valve catheter 58 includes a distal end 18 implanted within a spine 60 and a proximal end 16 coupled to an implanted pump 54. Catheter 58 further includes at least one slit valve, conforming to any of the embodiments described herein, near distal end 18 for delivery of therapeutic agents or nutrients from pump 54 to spine 60.

Figure 7:
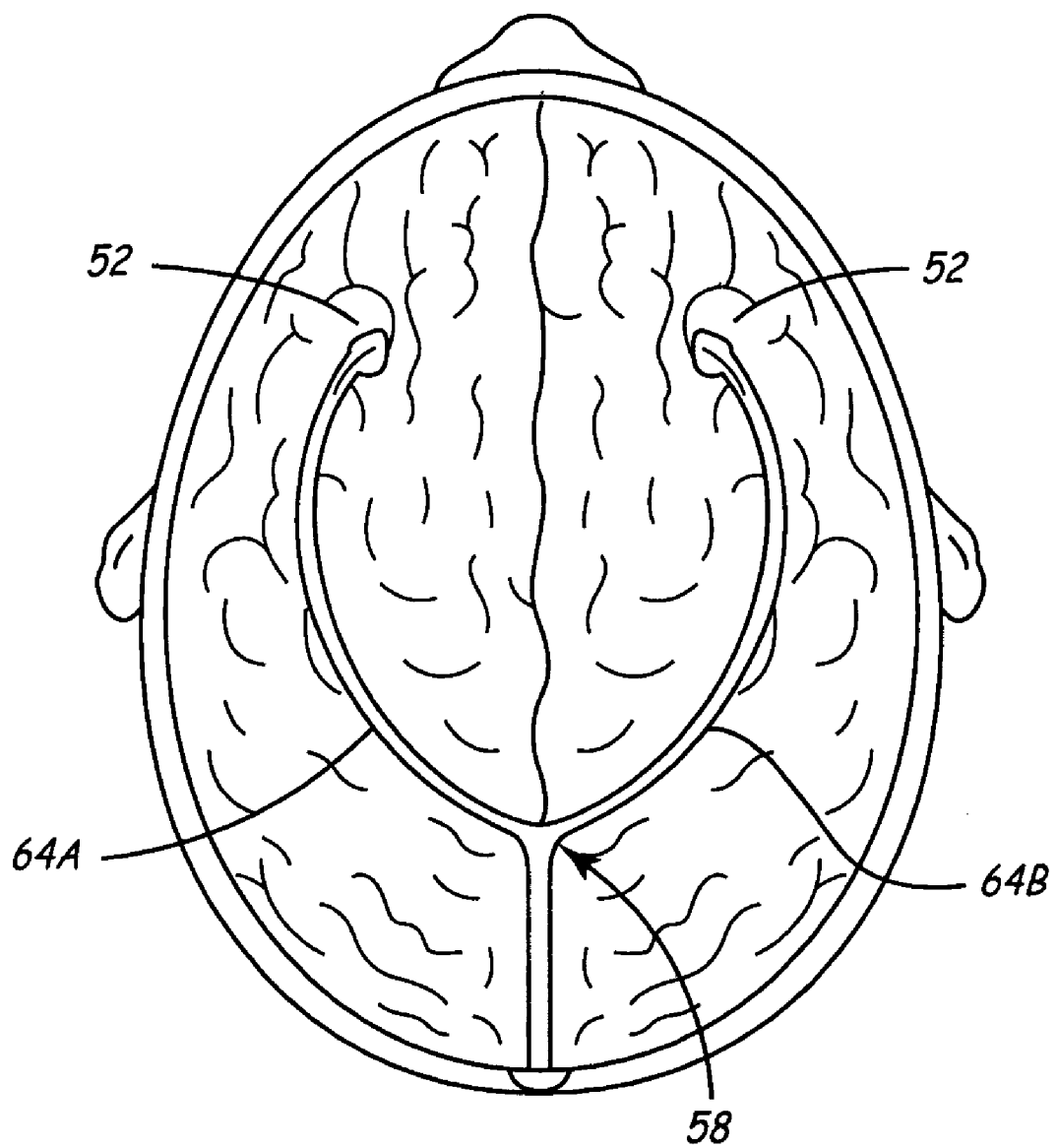
FIG. 7 is a schematic diagram illustrating a distal end of the implanted catheter of FIG. 5.

FIG. 7 is a schematic diagram illustrating a distal end of the implanted catheter of FIG. 5. As illustrated in FIG. 7, distal end 18 of sleeve valve catheter 58 includes branches 64A and 64B, each branch including at least one slit valve, conforming to any of the embodiments described herein.

Various embodiments of the invention have been described. Various modifications may be made without departing from the scope of the claims. The techniques of the invention may, for example, be applied to a catheter that has a sleeve valve in addition to a slit valve. For example, the slit valve may function as the primary valve and the sleeve valve may function as the surrogate valve. Further, the techniques of the invention may be applied to a multi-lumen catheter. For example, a first lumen within the multi-lumen catheter may be associated with a first slit valve and a second lumen within the multi-lumen catheter may be associated with a second slit valve. The slits associated with the first and second lumens may be related only to their respective lumens such that the fluids of the lumens do not interact with one another within the catheter. These and other embodiments are within the scope of the following claims.

The invention claimed is:

1. A medical device comprising a catheter, the catheter comprising:
   a catheter body having a closed end, distal tip portion with an exterior surface;
   the distal tip portion comprising a wall circumscribing a single lumen;
   the wall defining the shape of the exterior surface of the distal tip portion;
   the wall having a slit portion having a pressure responsive slit in the exterior surface of the distal tip portion and extending through the portion of the wall of the distal tip portion with a first wall thickness, the slit being substantially aligned with a longitudinal axis of the distal tip portion and extending through the wall of the distal tip at an angle of orientation, the slit extending the length of the slit portion;
   the slit portion having an indentation in the exterior surface defined by the wall and having the first wall thickness, the slit being within the indentation;
   the wall having a portion on one side of the slit with a second wall thickness that is greater than the first wall thickness and defining a first discrete ridge on the exterior surface of the distal tip portion;
   the wall having a portion on the opposite side of the slit with substantially the same second wall thickness and defining a second discrete ridge on the exterior surface of the distal tip portion;
   the wall having a portion extending between the first and second discrete ridges with a wall thickness that is substantially the same as the first wall thickness,
   wherein the first and second discrete ridges are oriented to extend away from the lumen of the distal tip portion in a substantially parallel relationship to one another and to the angle of orientation at which the slit extends through the wall of the distal tip portion,
   wherein material exits the lumen, via the pressure responsive slit, when a pressure inside the lumen exceeds an external pressure.

2. The medical device of claim 1, wherein the catheter body proximate the slit is chemically treated.

3. The medical device of claim 1, wherein a compliance of the catheter body proximate the slit is greater than a compliance of a major portion of the catheter body.

4. The medical device of claim 1, wherein the indentation comprises a plurality of indentations and the slit comprises a plurality of slits.

5. The medical device of claim 4, wherein each of the plurality of indentations and each of the plurality of slits is longitudinally displaced relative to one another along a length of the catheter body.

6. The medical device of claim 4, wherein each of the plurality of indentations and each of the plurality of slits is circumferentially displaced relative to one another along a length of the catheter body.

7. The medical device of claim 6, wherein each of the plurality of slits opens at a different pressure differential.

8. The medical device of claim 7, wherein each of the plurality of slits has a different length in order to open at the different pressure differential.

9. The medical device of claim 8, further comprising a distal end and wherein each of the plurality of slits is longitudinally displaced relative to one another along a length of the catheter body and the slits having a longer length are located toward a distal end of the catheter body.

10. The medical device of claim 1, wherein a second material enters the lumen, via the pressure responsive slit, when the external pressure exceeds the pressure inside the lumen.

11. The medical device of claim 1, further comprising a coating on the catheter body eluting a therapeutic agent.

12. The medical device of claim 11, wherein the therapeutic agent is at least one or combination of drugs, proteins, or genes having an anti-inflammation, anti-thrombus, anti-proliferation, and pro-healing effect at the catheter-tissue interface.

13. The medical device of claim 1, wherein the catheter body is formed from a material selected from the group consisting of silicone, polyurethane, polyimide, polyamide, polyethylene, polypropylene, and a fluoropolymer.

14. The medical device of claim 1, wherein the lumen defines a non-circular cross-section in an area proximate the pressure responsive slit when the external pressure equals or exceeds the pressure inside the lumen.

15. The medical device of claim 14, wherein the lumen defines a substantially circular cross-section in an area proximate the pressure responsive slit when the pressure inside the lumen exceeds the external pressure.

16. The medical device of claim 1, wherein the catheter body is formed from silicone, the slit includes two opposing surfaces, and further comprising a material spread on at least one of the two opposing surfaces to prevent blocking of the two opposing surfaces of the slit.

17. The medical device of claim 16, wherein the material to prevent blocking comprises one of graphite and talc.

18. The medical device of claim 4, wherein the catheter body further comprises a first and second branch and a first slit of the plurality of slits is formed in the first branch and a second slit of the plurality of slits is formed in the second branch.

19. The medical device of claim 4, wherein the lumen comprises a plurality of lumens and a first slit of the plurality of slits corresponds with a first lumen of the plurality of lumens and a second slit of the plurality of slits corresponds with a second lumen of the plurality of lumens.

* * * * *